United States Patent [19]

McCain et al.

[11] 4,453,022

[45] Jun. 5, 1984

[54] PROCESS FOR PREPARING NONIONIC SURFACTANTS-OXYALKYLATION WITH CALCIUM AND/OR STRONTIUM CATALYSTS

[75] Inventors: James H. McCain; Louis F. Theiling, Jr., both of Charleston, W. Va.

[73] Assignee: Union Carbide Corporation, Danbury, Conn.

[21] Appl. No.: 370,204

[22] Filed: Apr. 21, 1982

[51] Int. Cl.$^3$ .............................................. C07C 41/03
[52] U.S. Cl. ..................................... 568/618; 568/619; 568/620; 568/623; 568/624; 568/625; 568/622
[58] Field of Search ............... 568/618, 619, 620, 622, 568/625

[56] References Cited

U.S. PATENT DOCUMENTS

| | | | |
|---|---|---|---|
| 3,100,750 | 8/1963 | Bailey et al. | 568/851 |
| 3,328,306 | 6/1967 | Ellis | 568/618 A X |
| 4,210,764 | 7/1980 | Yang et al. | 568/618 |
| 4,223,164 | 9/1980 | Yang et al. | 568/618 |
| 4,302,613 | 11/1981 | Yang et al. | 568/618 |

FOREIGN PATENT DOCUMENTS

| | | |
|---|---|---|
| 0034649 | 2/1981 | European Pat. Off. . |
| 0034648 | 2/1981 | European Pat. Off. . |
| 0026546 | 4/1981 | European Pat. Off. ............ 568/618 |

*Primary Examiner*—Howard T. Mars
*Attorney, Agent, or Firm*—Jean B. Mauro

[57] ABSTRACT

The process for preparing nonionic surfactants wherein a narrower molecular weight distribution is obtained by the use of a calcium and/or strontium catalyst which comprises reacting a reactive hydrogen compound selected from the group consisting of monohydric alcohols having from about 8 to about 20 carbon atoms and a difunctional polypropylene oxide polymer having an average molecular weight in the range of 1000 to 5000 with an alkylene oxide having 2 to 4 carbon atoms at a temperature at which the reaction proceeds in the presence of at least a catalytic amount of a basic salt of calcium and/or strontium selected from the group consisting of hydroxide, alkoxide and phenoxides and a catalytic amount of an oxyalkylation catalyst promoter.

8 Claims, No Drawings

PROCESS FOR PREPARING NONIONIC SURFACTANTS-OXYALKYLATION WITH CALCIUM AND/OR STRONTIUM CATALYSTS

DESCRIPTION

1. Field Of The Invention

The present invention relates to a process for the preparation of nonionic surfactants wherein the molecular weight distribution of the nonionic surfactants obtained is narrower than that obtained by use of a calcium and/or strontium oxyalkylation catalyst wherein the oxyalkylation promoter of this invention is not employed.

2. Background Of The Invention

The instant invention relates to the preparation of improved nonionic surface active agents and, more particularly, to a process for the oxyalkylation of certain reactive hydrogen compounds to prepare nonionic surface active agents having lower pour points wherein the molecular weight distribution is narrower than that obtained with catalysts employed heretofore.

Low molecular weight condensation products of an alkylene oxide, particularly ethylene oxide, or mixtures of alkylene oxides such as ethylene and propylene oxide with an alcohol are well known and for a long time have been prepared commercially for use in detergents, cleansing agents, dry cleaning materials, wetting and emulsifying agents and the like. These products are conventionally produced by reacting the reactive hydrogen compound with the alkylene oxide in the presence of a strongly alkaline or an acidic catalyst. Such preparative procedures result in the production of a mixture of relatively low molecular weight (up to about 5000) condensation product species containing a number of alcohol derivatives having different molecular proportions of alkoxylate. Thus, the reaction products generally obtained are, in reality, a mixture of derivatives of the alcohol moiety containing different molecular proportions of alkylene oxide units, i.e., having varying molar ratios of alcohol to alkylene oxide, and a wide range of molecular weights as well as having a certain proportion of unreacted alcohol. Moreover, as is well known, the conventional designation of the number of alkylene oxide units present per molecule of an alcohol alkoxylate is a designation of the average number of alkylene oxide units per molecule and that a substantial proportion of the alcohol alkoxylates present are present as alcohol alkoxylates having a greater and a lesser number of alkylene oxide units present than the actual average value would indicate. Such designations of such products is well understood in the art and will be employed herein consistent with is well understood meaning.

It is generally desirable to restrict, i.e. control the breath of the molecular weight distribution of the mixture to adjacent analogues of the desired product insofar as possible, since, as is well known, the number of moles of alkylene oxide in the reaction product is a major factor in determining what the properties of such products are, but as a matter of course it is quite difficult to control the molecular weight distribution. Acidic catalysts tend to give a narrower molecular distribution than alkaline catalysts, but, unfortunately, also contribute to the formation of undesired by-products. Thus, alkaline catalysts which are typically a strong base such as alkali metal hydroxides and alcoholates are generally used as the more efficient type of oxyalkylation catalyst, but the molecular distribution of the products are more diffuse, containing a greater proportion of lower and higher molecular weight species and smaller amounts of the species with the desired number of moles of alkylene oxide per mole of alcohol. For example, an 8-mole ethylene oxide (EO) adduct per mole of 1-dodecanol will contain not only the 8-mole EO adduct specie but also lower mole adducts and higher mole adducts. Lower mole adducts in the product mixture will range down to the one-mole adduct and higher adducts will extend up to 14 or 15 and beyond. The molecular weight distribution is a measure of the relative amounts of the various adducts in the product mixture and can be represented in the form of a generally bell-shaped curve where the amount of each adduct species is plotted versus the number of moles of epoxide in the specie or of a description of the relative amount of each individual adduct. When the molecular weight distribution is characterized by a bell-shaped curve, a narrower distribution gives a sharper curve which is, higher at the middle and lower at the ends. A broader distribution curve would be lower at the middle portion of the range and higher at the ends, and such is not desirable.

Heretofore, several methods have been suggested for providing reaction products of an active hydrogen compound, e.g., alcohol, and epoxides which have a narrower range of molecular weights and molecular distribution of the epoxide units, and/or which reduce or eliminate the production of undesirable poly(alkylene glycol) and cyclic and straight chain ether by-products. For example, in U.S. Pat. No. 4,112,231 to Weibull et al it is disclosed that the use of certain neutral inorganic fluoborate and perchlorate salts will catalyze the reaction of epoxides with active hydrogen compounds to give products having a relatively narrower molecular distribution, i.e., a more limited range of molecular species and a larger proportion of desired molecular species; in U.S. Pat. No. 3,682,849 to Smith et al improved ethoxylated derivatives of $C_{11}$–$C_{18}$ alcohols are prepared by removing unreacted alcohol and lower ethoxylates from the ethoxylate mixture prepared by conventional methods by use of vapor phase separation techniques; in U.S. Pat. No. 2,870,220 to Carter, a two-stage process is disclosed for preparing monoalkyl ethers of ethylene glycol and polyethylene glycols of more restricted molecular weight range wherein an alkanol and ethylene oxide is reacted in the presence of an acidic catalyst during the first stage and then in the second-stage after removal of acid catalyst and unreacted alkanol, reacting the mixture with ethylene oxide in the presence of an alkali metal alcoholate of the initial alkanol; and in United Kingdom Pat. No. 1,501,327 to Laemmle et. al. there is disclosed a method of preparing mono- and poly-glycol ethers substantially free of undesired alkylene glycol by-products which method involves heating a reaction mixture containing an alkylene oxide and an alcohol in the presence of a catalyst containing alkali or alkaline earth cations wherein some or all of the catalyst is an anhydrous high boiling liquid residue prepared by concentrating the liquid residue from the same or different etherification processes after removal of the glycol ether product from the reaction mixture. None of the above-descirbed processes and special catalysts disclosed in the art, however, are completely satisfactory in preparing a product with a desired molecular distribution in that such generally require multi-stage procedures or special acid-resistant equipment, may form undesirable by-products or simply do not provide sufficient control over the molecular weight distribution to be of a satisfactory nature. Thus, it would be highly desirable to develop a process wherein the reaction of an alkylene oxide (epoxide) with an alcohol could be more readily carried out to prepare surfactant products that have a relatively narrower molecular weight distribution of anologue species and contain only small amounts, at most, of undesirable poly(alkylene glycol) and ether by-products.

Recently, several patents were issued which are concerned with the preparation and advantages of nonionic surfactant products having a narrower molecular weight distribution. For example, U.S. Pat. No. 4,239,917 to Yang discloses the use of a class of basic barium materials as catalysts in the preparation of reaction products of alcohols and ethylene oxide so as to provide a product with a narrow, high mole adduct distribution while providing relatively low levels of undesirable by-products and unreacted free alcohol. The molecular weight distribution factor of the products produced during the oxyalkylation reaction is discussed at length by patentee and the differences in the molecular weight distribution of reaction products prepared with conventional alkali metal catalysts such as sodium hydroxide and those prepared using a barium catalyst of the invention is shown by graphical representations. The patent, to Yang, also shows that other alkaline earth metal materials, such as calcium hydroxide, magnesium oxide, and strontium hydroxide, were ineffective as catalysts for the oxyalkylation reaction. Thus patentee demonstrates that significant differences exist in catalytic effectiveness even between the various alkaline earth metals and not only between the barium catalysts of the invention and alkali metal hydroxides.

Further, U.S. Pat. No. 4,210,764 and 4,223,164 to Yang et al are concerned with the problem of the molecular weight distribution of products prepared by oxyalklyation of alcohols using conventional alkaline catalysts and are directed to overcoming an induction period problem frequently observed when employing barium-containing catalysts, such as those disclosed in U.S. Pat. No. 4,239,917. The patentees suggest the use of various phenols for use as a promoter for the barium-containing catalyst to overcome the induction period difficulty, and U.S. Patent 4,223,164, disclose that with such promoters, certain basic strontium materials may also be employed as a catalyst for the oxyalkylation reaction.

Thus the above-discussed patents have disclosed pronounced differences in catalytic activity between the various alkaline earth metals and alkaline materials in general during the reaction of alkylene oxides with alcohols as well as the significant differences in the products prepared using a conventional alkali metal catalysts relative to those products prepared in the presence of alkaline earth metal materials which exhibit catalytic activity. The detailed discussion by patentees concerning controls of the molecular weight distribution of the products prepared during the oxyalkylation reaction serves to detail the differences that exist between those products which are obtained by careful catalyst selection and the differences in product properties that may be realized by simply employing varying proportions of alkylene oxide in the reaction.

A process for preparing nonionic surfactants having a relatively narrower molecular weight distribution is disclosed in copending U.S. Ser. No. 079,539, filed Sept. 27, 1979, wherein nonionic surfactants are prepared by use of a basic salt of an alkaline earth metal selected from the group consisting of calcium, strontium, and barium alkoxides, calcium, strontium, and barium phenoxides and mixtures of the same. A process is disclosed in copending U.S. Ser. No. 275,031, filed June 18, 1981, wherein a soluble basic salt of barium is prepared for use as an oxyalkylation catalyst. These processes are to be distinguished from the instant invention wherein oxyalkylation catalyst promoters are employed with a calcium and/or strontium catalyst to obtain a product with a relatively narrower molecular weight distribution.

SUMMARY OF THE INVENTION

In accordance with the present invention there is provided a process and the catalyst for carrying out the process for the preparation of nonionic surfactants having a molecular weight distribution which is narrower than that normally obtained by the use of a calcium and/or strontium catalyst. The process comprises reacting a reactive hydrogen compound selected from the group consisting of monohydric alcohols having between about 8 and about 25 carbon atoms, both branched and linear, and a difunctional polypropylene oxide polymer having an average molecular weight in the range of 1000 to 5000 with an alkylene oxide having 2 to 4 carbon atoms at a temperature at which the reaction proceeds in the presence of at least a catalytic amount of a basic salt of calcium and/or strontium wherein the basic salt is at least one of a hydroxide, alkoxides, phenoxides, or mixtures thereof and an acid compound (oxyalkylation promoter) as discussed hereinafter. Preferably the basic salt and oxyalkylation promoter are soluble in the reactants and the reaction products.

It has been discovered that the use of a basic salt of calcium and/or strontium, when employed as oxyalkylation catalyst as hereinafter described, with certain oxyalkylation catalyst promoter, as hereinafter described, provide an oxyalkylation catalyst that not only catalyzes the reaction of the active hydrogen compound with the alkylene oxide but also result in the formation of products having a narrower molecular distribution, i.e., a more limited range of molecular species and a larger proportion of the desired species in the reaction product than that which is prepared with conventional alkali metal catalysts such as potassium hydroxide and that which is prepared by use of only the basic salt of calcium and/or strontium as the oxyalkylation catalyst. In addition in many instances the rate to products, i.e., surface active agents is increased relative to those observed for conventional alkali metal catalyst and the basic salts of calcium and/or strontium. Moreover, the process of the instant invention can be readily carried out in a single stage with substantially no delay or induction period, and without the need for special acid-resistant preparatory equipment. The products produced thereby have been found, in general, to exhibit improved properties such as lower pour points and to contain relatively small amounts of undesired poly(alkylene glycol) and ether by products, such as those which are normally formed when acid compounds are used as the oxyalkylation catalyst.

DETAILED DESCRIPTION OF THE INVENTION

The process of the invention comprises reacting a reactive hydrogen compound selected from the group consisting of monohydric alcohols having between about 8 and about 25 carbon atoms, more preferably between about 8 and about 20 carbon atoms and/or a difunctional polypropylene oxide polymer having an average molecular weight in the range of 1000 to 5000 with an alkylene oxide having 2 to 4 carbon atoms in the presence of an oxyalkylation catalyst comprising a catalytically effective amount of an alkoxides and/or phenoxides of calcium and/or strontium and mixtures thereof and a catalytically effective amount of an acid compound (oxyalkylation promoter) and salts thereof such as super phosphoric acid, phosphoric acid, diphosphoric acid, triphosphoric acid, phosphorous acid, dihydrogen phosphate compounds, oxides of phosphorous (e.g. $P_2O_5$, $P_2O_3$), sulfuric acid, bisulfate compounds, carbon dioxide, oxalic acid, and salts of oxalic acid as hereinafter more fully discussed. The salt of such acid compounds are believed to provide the poly-functional anion of the acid compound in situ, although the exact nature of the in situ reaction is not clearly understood.

The reaction may be conducted in a conventional manner, that is, the reactive hydrogen compound and the oxyalkylation catalyst (the term "oxyalkylation catalyst" is meant to include both the use of a catalyst of the instant invention wherein an oxyalkylation catalyst promoter, as hereinbefore defined, is employed and those compounds previously employed in the art as oryalkylation catalysts) are placed in a reactor, the selected alkylene oxide is added to the reaction mixture until the desired number of moles have been reacted with the reactive hydrogen compound, and the product is removed from the reactor and neutralized. The reaction may be conducted in the presence of a solvent, but usually a solvent is not necessarily employed. The process may be carried in a batch manner or in a continuous mode of operation.

The temperature at which the reaction proceeds is not narrowly critical and generally products can be made at a reasonable rate of reaction and without decomposition of the reactants or reaction products at a temperature between about 50° C. and about 400° C., with a temperature between about 100° C. and about 200° C. being generally preferred. While the pressure of the reaction is not narrowly critical when low-boiling epoxides, such as ethylene oxide and propylene oxide are employed, a pressurized reactor is preferably used. The ethylene oxide pressure, in general, depends on the selected temperature and the amount of unreacted ethylene oxide with a pressure between about 10 psig and about 100 psig being generally preferred.

The reaction product may be neutralized with any acid that will convert the oxyalkylation catalyst to a neutral salt, as for example, acetic acid, or additional quantities of carbon dioxide, sulfuric acid, and/or phosphoric acid.

Alcohols which are suitable for use in the practice of the invention as the reactive hydrogen compound are primary and secondary aliphatic alcohols which are straight or branched chain and have between about four and about twenty five carbon atoms. Exemplary of such alcohols are those derived by hydrogenation of natural fats and oils, such as CO and TA alcohols, trademark of and soldy by Proctor and Gamble Co., such as CO-1214N alcohol, CO-1618 alcohol, and TA 1618 alcohol, and ADOL alcohols, trademark of and sold by Ashland Oil Co., such as ADOL 54 alcohol, ADOL 61 alcohol, ADOL 64 alcohol, ADOL 60 alcohol and ADOL 66 alcohol. Alcohols produced by Ziegler chemistry can also be alkoxylated. Examples of these alcohols are ALFOL alcohols, trademarks of and sold by Continental Oil Co., such as ALFOL 1012 alcohol, ALFOL 1214 alcohol, ALFOL 1412 alcohol, ALFOL 1618 alcohol, ALFOL 1620 alcohol; and EPAL alcohols, trademark of and sold by Ethyl Chemical Co., such as EPAL 1012 alcohol, EPAL 1214 alcohol, EPAL 1418 alcohol. The invention is extremely useful for oxo alcohols (hydroformylation) produced from olefins. Examples of such alcohols are NEODOL alcohol, trademark of and sold by Shell Oil Col, such as NEODOL 23 alcohol, NEODOL 25 alcohol, NEODOL 1418 alcohol; TERGITOL-L, trademark of Union Carbide Corp., such as TERGITOL-L 125 alcohol; LIAL alcohols, trademark of and sold by Liquichimica Co. such as LIAL 125; and isodecyl and tridecyl alcohols, sold by Exxon Corp., such as isodecyl alcohol and tridecyl alcohol, Guebet alcohols can also be ethoxylated. Representative examples of these alcohols are STANDAMUL alcohols, trademark of and sold by Henkel Chemical Co., such as STANDAMUL GT-12 alcohol, STANDAMUL GT-16 alcohol, STANDAMUL GT-20 alcohol, STANDAMUL GT-1620 alcohol. Secondary alcohols can also be used, such as TERGITOL 15 alcohol, trademark of and sold by Union Carbide Corp.

Generally, useable alcohols include 1-decanol; 1-undecanol; 1-dodecanol; 1-tricecanol; 1-tetradecanol; 1-pentadecanol; 1-hexadecanol; 1-heptadecanol; 1-octadecanol; 1-nonadecanol; 1-eicosanol; 1-dicosanol; 2-methyl-1-undecanol 2-propyl-1-nonanol; 2-butyl-1-octanol; 2-methyl-1-tridecanol; 2-ethyl-1-dodecanol; 2-propyl-1-undecanol; 2-butyl-1-decanol; 2-pentyl-1-nonanol; 2-hexyl-1-octanol; 2-methyl-1-pentadecanol; 2-ethyl-1-tetradecanol; 2-propyl-1-tridecanol; 2-butyl-1-dodecanol; 2-pentyl-1-undecanol; 2-hexyl-1-decanol; 2-heptyl-1-decanol; 2-hexyl-1-nonanol; 2-octyl-1-octanol; 2-methyl-1-heptadecanol; 2-ethyl-1-hexadecanol; 2-propyl-1-pentadecanol; 2-butyl-1-tetradecanol; 1-pentyl-1-tridecanol; 2-hexyl-1-dodecanol; 2-octyl-1-decanol; 2-nonyl-1-nonanol; 2-dodecanol; 3-dodecanol; 4-dodecanol; 5-dodecanol; 6-dodecanol; 2-tetradecanol; 3-tetradecanol; 4-tetradecanol; 5-tetradecanol; 6-tetradecanol; tetradecanol; 7-tetradecanol; 2-hexadecanol; 3-hexadecanol; 4-hexadecanol; 5-hexadecanol; 6-hexadecanol; 7-hexadecanol; 8-hexadecanol; 2-octadecanol; 3-octadecanol; 3-octadecanol; 4-octadecanol; 5-octadecanol; 6-octadecanol; 7-octadecanol; 8-octadecanol; 9-octadecanol; 9-octadecanol-1; 2,4,6-trimethyl-1-heptanol; 2,4,6,8-tetramethyl-1-nonanol; 3,5,5-trimethyl-1-hexanol; 3,5,5,7,7-pentamethyl-1-octanol; 3-butyl-1-nonanol; 3butyl-1-; undecanol; 3-hexyl-1-hexyl-1-undecanol; 3-hexyl-1tridecanol; 3-octyl-1-tridecanol; 2-methyl-2-undecanol; 3-methyl-3-undecanol; 4-methyl-4-undecanol; 2-methyl-2-tridecanol; 3-methyl-3-tridecanol; 4-methyl-3-tridecanol; 4methyl-4-tridecanol; 3-ethyl-3-decanol; 3-ethyl-3-dodecanol; 2,4,6,8-tetramethyl-2-non-anol; 2-methyl-3-undecanol; 2-methyl-4-undecanol; 4-methyl-2-undecanol; 5-methyl-2-undecanol; 4-ethyl-2-decanol; 4-ethyl-3-decanol.

Also employable as the reactive hydrogen compound are the difunctional propylene oxide polymers having a molecular weight of 1000 to 5000, and preferably 1700 to 4100. The propylene oxide polymers having a molecular weight of 1000 to 5000 contain from 17 to 86 oxypropylene units in the molecular. These compounds are well known, being generally obtained by polymerization of propylene oxide or by the addition of propylene oxide to lower molecular compounds with 2 to 6 carbon atoms containing at least 2 reactive hydrogen atoms.

Alkylene oxides which may be employed in accordance with the invention include those alkylene oxides having between about 2 and about 4 carbon atoms and include, for example, ethylene oxide, 1,2-propylene oxide, and butylene oxides such as 1,2-butylene oxide, and mixtures thereof. The number of moles of alkylene oxides employed according to the present invention may vary widely depending on the reactive hydrogen compound to be adducted and the particular application for which the surface active agent is to be employed. In general between about 2 and about 80 or greater moles of alkylene oxide per mole of reactive hydrogen compound may be employed with greater molar ratios being employed if higher molecular weight products are desired. Insofar as propylene oxide and/or butylene oxide are used in combination with ethylene oxide, the molar ratio of ethylene oxide to propylene oxide—or butylene oxide may be between about 50:1 and about 1:50, preferably between 3:1 to 1:3.

In the process of the invention, the reaction of an alkylene oxide with a reactive hydrogen compound is carried out in the presence of an oxyalkylation catalyst comprising a catalytic effective amount of a basic salt of calcium and/or strontium and mixtures thereof which are preferably soluble in the reactants and the reaction products produced thereby. However, for practical reasons, preferably between about 0.1 and about 0.1 weight percent is employed, based upon the weight of the alcohol to be reacted. Suitable basic salts of calcium and strontium include the alkoxides, especially those alkoxides having alcohol moieties which are the same or similar to the reactive hydrogen compound component of the oxyalkylation reaction or have an alcohol moiety having at least about 8 carbon atoms, and phenoxides.

While the basic salts of calcium and strontium suitable for use in accordance with the invention may be prepared by those methods known in the art, a particularly preferred basic salt for use as a catalyst in the invention is prepared by the method disclosed in copending application United States Ser. No. 079,497 wherein calcium, strontium and barium alkoxides of higher alcohols having more than 4 carbon atoms, and particularly, having an alcohol moiety that is the same or similar to the alcohol reactive hydrogen component are disclosed.

Metal alkoxides are, in general, prepared by a two step process. In the first step of the process, for example, calcium and strontium containing raw materials such as calcium and strontium metal, or hydrides or acetylides are reacted with a lower aliphatic alcohol having between about 4 and about 25 carbon atoms. The concentration of metal in the lower alcohol may vary from 0.01 to 20 percent. In the second step, the lower alcohol metal alkoxide reaction product is mixed with a higher alcohol having at least 4, and preferably at least 8, carbon atoms to form the metal alkoxide thereof which is employed to provide the catalyst for the oxyalkylation reaction. The metal alkoxide prepared thereby preferably has an alcohol moiety which is the same or similar to the reactive hydrogen component used in the oxyalkylation reaction mixture and is soluble in said reactive hydrogen component. The lower alcohol (alcohol having between about 4 and about 25 carbon atoms) introduced with the lower metal alkoxide is removed from the final metal alkoxide reaction product by any separation means that retains the catalytic activity of the metal alkoxide (i.e., the calcium or strontium alkoxide) with distillation being the generally preferred means of separation.

Phenoxides of calcium and strontium which are suitable for use in accordance with the invention may be prepared by reacting phenols with the certain basic salts of calcium and/or strontium such as their alkoxides. Preferably the phenoxide is prepared by adding the phenol to the lower alcohol-metal alkoxide, prepared as abovedescribed. The amount of the phenol added is not narrowly critical. It can vary from a few hundredths of a molar equivalent based on alkoxide to several equivalents. Illustrative of phenols suitable for use are phenol, orthocresol, metacresol, paracresol, 2,4-dialkylphenols, 2,5-dialkylphenols, nonylphenol, octylphenol, hydroquinone, and pyrogallol.

The term "acid compounds" as used herein is synonomous with in conjunction with the term "oxyalkylation catalyst promoter" and the term is used herein to refer to the group of oxyalkylation catalyst promoters selected from the group consisting of superphosphoric acid, phosphoric acid, sulfuric acid, alkali metal and alkaline earth metal dihydrogen phosphates, alkali metal and alkaline earth metal dihydrogen diphosphates, alkyl, aryl, araalkyl and alkylaryl dihydrogen phosphates, monoalkyl hydrogen sulfates, carbonic acid, carbon dioxide, alkali metal bicarbonates, oxalic acid, alkali metal and alkaline earth metal oxalates, oxides of phosphorus, including phosphorous pentoxide, diphosphorus trioxide, sulfur trioxide, sulfur dioxide, and sulfurous acid. When the acid compound is an alkyl dihydrogen phosphate, dihydrogen diphosphate and/or an alkyl hydrogen sulfate the alkyl preferably contains between 1 and about 25 carbon atoms, preferably between 1 and about 10 carbon atoms, and may be branched or linear.

The oxyalkylation catalyst used in accordance with the invention consists of a calcium and/or strontium basic salt and an oxyalkylation catalyst promoter (hereinafter promoter) and the amount is not narrowly critical with a catalytic effect having been observed employing only small amounts of basic salts of calcium and strontium and of the promotor. In general, the concentration of acid compound can vary between about 0.001 percent by weight and about 10 percent by weight of calcium and/or strontium based on the weight of active hydrogen compound employed. Concentrations of calcium and/or strontium within the range between about 0.05 percent and about 5.0 percent by weight of active hydrogen compound are usually preferred. The amount of acid compound employed is not narrowly critical and a catalytic effect has been observed employing only small amounts of (catalytically effective amount) the acid compound in conjunction with the basic salts of calcium and/or strontium. The reaction rate, however, is generally dependent on both the process temperature and the concentration of the basic salts of calcium and/or strontium and the concentration of the promoter employed. In general, to achieve a given rate, more catalyst is required at a low process temperature than that which is required at a higher process temperature. The solubility of the calcium and strontium basic salts and the promoter in the reaction mixture is also an important factor in achieving a suitable reaction rate and preventing a long induction period, and preferably, are substantially soluble in the reaction mixture. Basic salts of calcium and/or strontium and promoter(s) that are only partially soluble in the reaction mixture at ambient conditions or at the process temperature however, may be suitable if the soluble portion provides a catalytically effective concentration of calcium and/or strontium and the promoter(s).

The products prepared by the reaction of the reactive hydrogen compound and the alkylene oxide, in accordance with the practice of the invention, are, in general, a mixture of relatively low molecular weight alkoxylates (molecular weight up to about 5000) which are efficient nonionic surfactants wherein the molecular weight distribution of the alkoxylate species in the mixture is narrower than that obtained using conventional alkali metal catalysts such as potassium hydroxide or by use of only the basic salts of calcium or strontium without an oxyalkylation catalyst promoter. Thus, the alkoxylate products are prepared having a greater proportion of the desired alkoxylate species, that is, having a greater proportion of products with the desired number of alkylene oxide groups per mole of active hydrogen compounds, e.g., alcohol. Moreover, products prepared in accordance with the invention generally have a smaller amount of unreacted alcohol and have a smaller amount of the undesirable poly(alkylene glycol) by-products formed. In addition, the products generally exhibit improved properties, such as a lower pour points, as compared to products prepared by the reaction of comparable amounts of alkylene oxide and alcohol reactants in the presence of conventional alkaline catalysts or solely with a basic salt of calcium and/or strontium.

The invention will become more clear when considered together with the following examples which are set forth as being merely illustrative of the invention and which are not intended, in any manner, to be limitative thereof. Unless otherwise indicated, all parts and percentages are by weight.

EXPERIMENTAL PROCEDURE

All examples except as noted were carried out in a 2.0 gallon stirred stainless steel autoclave equipped with automatic temperature and pressure controllers. The selected alcohol and catalyst were placed in the autoclave at room temperature and purged three times with nitrogen. The reactor was heated to the reaction temperature and then pressurized to 20 psig with nitrogen. Alkylene oxide was added from a calibrated tank until the pressure reached about 60 psig (pounds per square inch). Thereafter, as alkylene oxide reacted and the pressure fell, more alkylene oxide was automatically added to maintain the alkylene pressure at about 60 psig. When the desired amount of oxide had been added, the feed tank was valved off and the pressure was allowed to fall. When constant pressure was reached, the reactor was cooled and discharged. Generally the final products were neutralized to pH 7 with acetic acid or phosphoric acid and filtered. The product was derivatized with a silane (trimethylsilyl derivative) before analysis by vapor phase, i.e., gas chromatography. The gas chromatographic analysis was carried out on a Hewlett Packard Model No. 5830A equipped with a flame ionization detector. The column consisted of a 4 foot×⅛ inch (O.D.) stainless steel column packed with Chromosorb (Trademark of Johns-Manville Filtration and Materials Div.) which had been acid washed and DMCS (treated) prior to Application of 2% OV-1 (Trademark of Ohio Valley Specialty Chemical Co.). The analysis was carried out using a 1.1 microliter sample size with helium as the carrier gas (flow rate of 25 cubic centimeters/minute) with the column temperature increasing during analysis from about 70° C. to about 340° C. at the rate of about 3° C. per minute.

EXAMPLE 1

Calcium ethoxide was prepared by reacting calcium metal (2.4 grams) with ethanol (100 milliliter) after which 2-ethylhexanol (500 grams) was added and the mixture heated at 70° C. at a pressure of 5 millimeters until substantially all the ethanol had been removed. The resulting mixture contained 0.142 moles of calcium alkoxide per 1000 grams of mixture.

To the mixture of calcium alkoxide and 2-ethylhexanol was added phosphoric acid (2.25 grams, 0.023 moles) while the mixture was stirred. A portion of the resulting mixture (481 grams) was placed in the autoclave and reacted at 140° C. with ethylene oxide while the pressure was maintained at 60 psig by addition of ethylene oxide when the pressure fell below 60 psig. When the amount of reacted ethylene oxide corresponded to the desired average mole ratio of ethylene oxide per mole of alcohol was reacted the autoclave was cooled and the product neutralized with acid to a pH of about 7. In the instant example the reaction took place over a period of about 121 minutes with 1225 milliliters (ml) of ethylene oxide being consumed in the reaction (density at 20° C. of 0.865 grams per cubic centimeter). The product, a poly(ethylene oxide) adduct of 2-ethylhexanol, had a molecular weight of 422 and a 1 percent aqueous solution had a cloud point of 65° C. The analysis (based on the moles of ethylene oxide per mole of alcohol) of the trimethylsilyl derivative is shown in Table I.

EXAMPLE 2

This is a comparative example showing the broad molecular weight distribution obtained when only a strong base catalyst is employed. To 2-ethylhexanol (500 grams) was added sodium hydroxide (3.01 grams) after which the mixture was heated at 70° C. to effect the reaction. The mixture was reacted with ethylene oxide according to the procedure of Example 1. Over a period of 60 minutes 1260 cubic centimeters of ethylene oxide reacted, giving a product having a molecular weight of 466. The cloud point (1 percent aqueous solution) was 72° C. Gas chromatographic analysis of the trimethylsily derivative gave the molecular weight distribution shown in Table I.

TABLE I

| Area Percent of Alcohol and Individual Ethylene Oxide Adducts of 2-Ethylhexanol | | |
|---|---|---|
| | Ex 1[b] 1 | Ex 2[b] 2 |
| Unreacted Alcohol Alcohol[a] | 9.4 | 17.2 |
| $E_1$ | 2.1 | 5.3 |
| $E_2$ | 1.3 | 6.0 |
| $E_3$ | 6.6 | 7.1 |
| $E_4$ | 9.4 | 7.0 |
| $E_5$ | 12.3 | 7.6 |
| $E_6$ | 14.0 | 7.7 |
| $E_7$ | 12.9 | 7.8 |
| $E_8$ | 11.5 | 7.3 |
| $E_9$ | 8.5 | 6.7 |
| $E_{10}$ | 5.7 | 5.6 |
| $E_{11}$ | 3.5 | 4.7 |
| $E_{12}$ | 1.8 | 4.2 |

TABLE I-continued

| Area Percent of Alcohol and Individual Ethylene Oxide Adducts of 2-Ethylhexanol | | |
|---|---|---|
| | Ex 1[b] | Ex 2[b] |
| | 1 | 2 |
| $E_{13}$ | 0.8 | 3.6 |
| $E_{14}$ | 0.3 | 3.1 |
| $E_{15}$ | | 2.6 |
| $E_{16}$ | | 2.2 |
| $E_{17}$ | | 1.7 |

[a]$E_1$ is the one-mole ethylene oxide adduct, $E_2$ is the two-mole ethylene oxide adduct, etc.
[b]given as an area percent.

EXAMPLE 3

This example shows the use of phosphoric acid as the oxyalkylation promoter with calcium alkoxide as the oxyalkylation catalyst. A total mixture containing 334 grams of 1-dodecanol and 0.272 moles of calcium alkoxide per 1000 of grams of the mixture was prepared by adding calcium ethoxide (in ethanol) to 1-dodecanol with removal therefrom of the ethanol in vacuo with the subsequent addition of 1-dodecanol (315 grams) to give a mixture containing 0.14 moles of calcium alkoxide per 1000 grams. To this mixture was added, with stirring, phosphoric acid (2.91 grams). The mixture was then heated at 110° C. under vacuum. A 598 gram aliquot of this mixture was employed according to the procedure of Example 1 with a total of about 1050 ml of ethylene oxide reacting over a period of about 97 minutes. The product, a poly(ethylene oxide) adduct of 1-dodecanol, had a molecular weight of about 457 and a cloud point (1 percent aqueous) of 55.5° C. Gas chromatographic analysis of the acetate derivative of the product gave the molecular weight distribution shown in Table II (this distribution should be compared with the broader molecular distribution of comparative example 5) showing a narrower molecular weight distribution of products than that obtained when the oxyalkylation promoters of the present invention are not employed.

EXAMPLE 4

This example illustrates the use of a higher concentration of phosphoric acid than employed in Example 3. A mixture containing 0.14 moles of calcium alkoxide per 1000 grams of mixture was added to dodecanol as in Example 3 (650 grams) and 4.48 grams of phosphoric acid was added with the resulting mixture being heated to 110° C. under a pressure of 35 mm. The autoclave and conditions of Example 1 were employed with an aliquot of the mixture (601 grams) reacting with 1075 milliter of ethylene oxide over a period of about 101 minutes. The product had a molecular weight of 509 and a cloud point (1 percent aqueous) of 65.5° C. Gas chromatographic analysis of the acetate derivative of the product gave the molecular distribution shown in Table II.

EXAMPLE 5

This is a comparative example employing calcium alkoxide as the oxyalkylation catalyst but without the use of phosphoric acid as a promoter. A 601 gram aliquot of a mixture containing 0.140 moles of calcium alkoxide per 1000 grams of the mixture was prepared as in Example 3 and was reacted with ethylene oxide in the autoclave and at the conditions set forth in Example 1. Over a 51 minute period 325 milliters of ethylene oxide reacted with the mixture and, a 203 gram sample of the product was taken. The reaction was carried out for an additional 146 minutes, with 575 milliters of ethylene oxide having been reacted. The total elapsed time for the reaction of 900 milliliters of ethylene oxide was 203 minutes. The final product had a molecular weight of 496 and a cloud point (1 percent aqueous) of 57.5° C. Gas chromatographic analysis of the acetate derivative of the product is set forth in Table II.

EXAMPLE 6

This example is a comparative example showing that phosphoric acid by itself is not effective as an oxyalkylation catalyst. Phosphoric acid (1.41 grams) was added to a one-liter flask containing 600 grams of 1-dodecanol with thorough mixing, and the oxyalkylation reaction was carried out according to the procedure of Example 1 with the mixture reacting with less than 60 millititers of ethylene oxide over a period of about 125 minutes.

EXAMPLE 7

This comparative example shows that the use of boric acid as a promoter with calcium alkoxide is not effective. To 1012 milliliters of ethanol in a stirred flask was added 32 grams of calcium metal (in shot form). The mixture was heated to reflux until the calcium metal had reacted. After the calcium metal had reacted 800 grams of 1-dodecanol was added and the ethanol removed by heating in the mixture in vacuo. The resulting mixture of calcium alkoxide in 1-dodecanol contained 1.24 moles of calcium per 1000 grams of the mixture.

An 85 gram aliquot of the mixture of calcium alkoxide in 1-dodecanol was added to 600 grams of 1-dodecanol to give a mixture containing 0.144 moles of calcium alkoxide per 1000 grams of the mixture. Boric acid was added to this mixture to (1.99 grams, 0.032 moles) with stirring. The oxyalkylation reaction was carried out according to the procedure of Example 1 with only 80 ml of ethylene oxide reacting over a period of 115 minutes.

EXAMPLE 8

This comparative example shows that the use of acetic acid as a promoter with calcium alkoxide is not effective as an oxyalkylation catalyst. To 614 grams of 1-dodecanol, containing 0.15 moles of calcium alkoxide per 1000 grams of mixture and prepared as in Example 7, was added 2.97 grams of acetic acid. The oxyalkylation was carried out as in Example 1 with only 65 milliliters of ethylene oxide reacting over a period of 120 minutes.

EXAMPLE 9

This comparative example shows that the use of benzoic acid as a promoter with calcium alkoxide is not effective as an oxyalkylation catalyst. To 600 grams of 1-dodecanol, containing 0.15 moles of calcium alkoxide per 1000 grams and prepared as in Example 7, was added 5.98 grams of benzoic acid. The reaction was carried out as in Example 1 with only 85 milliliters of ethylene oxide reacting over a period of 120 minutes.

EXAMPLE 10

This comparative example shows that the use of hydrogen chloride as a promoter with calcium alkoxide is not effective as an oxyalkylation catalyst. To 609 grams of 1-dodecanol, containing 0.15 moles of calcium alkoxide per 1000 grams (prepared as in Example 7), was added hydrogen chloride (1.65 grams, 0.045 moles). The reaction was carried out as in Example 1 with only 50 milliliters of ethylene oxide reacting over a period of 120 minutes.

EXAMPLE 11

This example shows the use of oxalic acid and calcium alkoxide provide an effective oxyalkylation catalyst according to the instant invention. To 610 grams of 1-dodecanol containing 0.15 moles of calcium alkoxide per 1000 grams of the mixture, (prepared as in Example 7), was added 2.25 grams of oxalic acid. The oxyalkylation reaction was carried out as in Example 1 with 945 milliliters of ethylene oxide reacting over a period of 159 minutes. The product had a molecular weight of 434 and a cloud point (1 percent aqueous) of 37.5° C. Gas chromatographic analysis of the trimethylsilyl derivative of the product gave the molecular distribution shown in Table II.

EXAMPLE 12

This example shows the use of carbon dioxide as an oxyalkylation promoter, according to the instant invention, and calcium alkoxide as an oxyalkylation catalyst. To 200 grams of a 1-dodecanol mixture containing 0.15 moles of calcium alkoxide per 1000 grams of the mixture (prepared as in Example 7), was added gaseous carbon dioxide until the pH of the mixture, measured with wet pH indicating paper, was between about 6 and 7. To 200 grams of the neutralized solution was added 400 grams of this mixture of 1-dodecanol and calcium alkoxide which had not been so neutralized. The oxyalkylation reaction was carried out as in Example 1 with 1040 milliliters of ethylene oxide reacting over a period of 104 minutes. The product had a molecular weight of 481 and a cloud point (1 percent aqueous) of 54° C. Gas chromatographic analysis of the trimethylsilyl derivative of the product is given in Table II.

EXAMPLE 13

This comparative example shows that calcium hydroxide is not effective with phosphoric acid as an oxyalkylation catalyst. 1-Dodecanol (600 grams), calcium hydroxide (6.45 grams, 0.87 moles) and phosphoric acid (2.78 grams, 0.029 moles) were mixed and stirred for one hour at 100° C. and at a pressure of 5 millimeters pressure. The mixture was then employed as an oxyalkylation catalyst in accordance with the procedure of Example 1. After a period of 120 minutes only 70 milliliters of ethylene oxide had reacted.

EXAMPLE 14

This comparative example shows that calcium oxide is not effective with phosphoric acid as an oxyalkylation catalyst. The procedure of Example 13 was repeated using calcium oxide (4.07 grams, 0.073 moles), 1-dodecanol (500 grams) and phosphoric acid (2.32 grams, 0.024 moles). After a period of 120 minutes, at 140° C., only 60 milliliters of ethylene oxide had reacted.

EXAMPLE 15

This comparative example shows the broad molecular distribution obtained when a strong base catalyst is employed as the oxyalkylation catalyst. To 1-dodecanol (525 grams) was added potassium hydroxide (12.69 grams; 33 percent aqueous solution) and the mixture was heated to 110° C. at a pressure of 5 millimeters pressure. An aliquot of the resulting mixture (500 grams) was employed in the oxyalkylation reaction as in Example 1 and reacted with 1080 milliliters of ethylene oxide over a period of 63 minutes. The product had a molecular weight of 495 grams and a cloud point (1 percent aqueous) of 55° C. The gas chromatographic analysis of the acetate derivative of the product is shown in Table II.

EXAMPLE 16

This comparative example shows that phosphoric acid has a deleterious effect on the formation rate of product when employed with a strong base catalyst(s). To 1-dodecanol (1200 grams) was added potassium hydroxide (11.09 grams as a powder). The resulting mixture was heated to 100° C. at a pressure of 5 milliliters. A 600 gram aliquot of the mixture was reacted with ethylene oxide according to Example 1 over a period of 130 minutes with 1065 milliliters of ethylene oxide reacting. The product had a molecular weight of 471 grams and a cloud point (1 percent aqueous) of 51° C. Gas chromatographic analysis of the acetate derivative of the product is shown in Table II.

TABLE II

| | Area Percent of Alcohol and Individual Ethylene Oxide Adducts of 1-Dodecanol | | | | | | |
|---|---|---|---|---|---|---|---|
| | Example[b] | | | | | | |
| | 3 | 4 | 5 | 11 | 12 | 15 | 16 |
| Unreacted Alcohol Alcohol[a] | 2.5 | 3.2 | 1.9 | 4.2 | 1.8 | 3.11 | 4.59 |
| $E_1$ | 0.9 | 0.5 | 2.1 | 3.1 | 1.3 | 3.73 | 3.66 |
| $E_2$ | 1.8 | 1.0 | 2.6 | 3.6 | 2.2 | 5.65 | 5.68 |
| $E_3$ | 4.2 | 2.3 | 4.8 | 7.5 | 5.0 | 8.01 | 7.95 |
| $E_4$ | 8.2 | 5.4 | 7.8 | 11.3 | 9.0 | 9.89 | 9.66 |
| $E_5$ | 13.3 | 10.3 | 10.9 | 15.5 | 14.4 | 11.20 | 10.64 |
| $E_6$ | 17.1 | 15.8 | 13.5 | 16.8 | 17.6 | 11.36 | 10.80 |
| $E_7$ | 17.3 | 18.1 | 14.6 | 15.1 | 17.1 | 11.29 | 10.60 |
| $E_8$ | 14.3 | 16.5 | 13.8 | 10.9 | 13.7 | 10.45 | 9.87 |
| $E_9$ | 10.0 | 12.6 | 11.5 | 6.7 | 9.1 | 8.98 | 8.64 |
| $E_{10}$ | 6.1 | 8.2 | 8.5 | 3.5 | 5.2 | 7.12 | 7.04 |
| $E_{11}$ | 3.0 | 4.3 | 5.5 | 1.5 | 2.5 | 5.06 | 5.22 |
| $E_{12}$ | 1.1 | 1.6 | 2.0 | 0.4 | 0.9 | 3.02 | 3.40 |
| $E_{13}$ | 0.2 | 0.3 | 0.6 | 0.1 | 0.2 | 1.20 | 1.73 |
| $E_{14}$ | | | | | | | 0.50 |
| $E_{15}$ | | | | | | | |
| $E_{16}$ | | | | | | | |
| $E_{17}$ | | | | | | | |

[a] $E_1$ is the one-mole ethylene oxide adduct, $E_2$ is the two-mole ethylene oxide adduct, etc.
[b] given as an area percent.

EXAMPLE 17

This is a comparative example, as in Example 5, showing the use of calcium alkoxide as the oxyalkylation catalyst, without added promoter. To a calcium ethoxide solution (prepared by reacting 32 grams calcium metal with 1012 milliliters of ethanol, at reflux) was added 800 grams of 1-dodecanol. The ethanol was removed at 100° C. and a pressure of 5 millmeters to give a product containing 1.16 moles of calcium alkoxide per 1000 grams of the mixture.. A 75 gram aliquot of this calcium alkoxide mixture was added to 1-dodecanol (525 grams) and reacted with ethylene oxide as in Example 1 with 146 minutes being required to react 1050 milliliters of ethylene oxide. The product had a molecular weight of 508 and a cloud point (1 percent aqueous) of 65.5° C. Gas chromatographic analysis of the trimethylsilyl derivative of the product gave the molecular distribution shown in Table III.

EXAMPLE 18

This example shows the use of phosphorous pentoxide as an oxyalkylation promoter, according to this invention, and calcium alkoxide as the oxyalkylation catalyst. To 75 grams of the calcium alkoxide solution prepared in Example 17 was added 1-dodecanol (525 grams) and phosphorous pentoxide (2.98 grams) while stirring and heating the mixture to 70° C. A 592 gram aliquot of the mixture was employed as Example 1 with 300 minutes being required to react 1050 milliliters of ethylene oxide. The molecular weight of the product was 503 and the cloud point (1 percent aqueous) was 63.5° C. Gas chromatograph analysis of the trimethylsilyl derivative of the product is shown in Table III.

EXAMPLE 19

This example shows the use of tributyl phosphate as the oxyalkylation promoter, according to this invention, and calcium alkoxide as the oxyalkylation catalyst. To 75 grams of the calcium alkoxide mixture prepared in Example 17 was added 525 grams of 1-dodecanol and 6.39 grams of tributylphosphate. The oxyalkylation reaction was carried out as in Example 1 with 275 minutes being required to react 1065 milliliters of ethylene oxide. The product had a molecular weight of 483 and a cloud point (1 percent aqueous) of 59° C. Gas chromatographic analysis of the trimethylsilyl derivative gave the molecular distribution shown in Table III.

EXAMPLE 20

This example shows the use of potasium dihydrogen phosphate as an oxyalkylation promoter, according to this invention, and calcium alkoxide as the oxyalkylation catalyst. The procedure of Example 19 was repeated except that instead of $P_2O_5$ the oxyalkylation promoter was $KH_2PO_4$ (8.17 grams). Ethylene oxide (1060 milliliters) reacted over a period of 150 minutes to give a product having a molecular weight of 466 and a cloud point (1 percent aqueous) of 57.5° C. Gas chromatographic analysis of the trimethylsilyl derivative gave the molecular distribution set forth in Table III.

EXAMPLE 21

This comparative example shows that the use of dipotassium hydrogen phosphate and calcium alkoxide is not effective as an oxyalkylation catalyst. The procedure of Example 19 was repeated except that instead of using $P_2O_5$, the oxyalkylation promoter was $K_2HPO_4 \cdot 3H_2O$ (18.03 grams) was used as the oxyalkylation promoter. Over a period of 360 minutes only 130 milliliters of ethylene oxide reacted showing that dipotassium hydrogen phosphate is not effective as an oxyalkylation promoter.

EXAMPLE 22

This example shows the use of sodium dihydrogen diphosphate as an oxyalkylation promoter, according to this invention, and calcium alkoxide as the oxyalkylation catalyst. The procedure of Example 19 was repeated except instead of $P_2O_5$, the oxyalkylation promoter was $Na_2H_2P_2O_7$ (4.23 grams). Over a period of 184 minutes ethylene oxide (1060 ml) reacted to give a product with a molecular weight of 509.5. Gas chromatographic analysis of the trimethylsilyl derivative of the product gave the molecular distribution set forth in Table III.

TABLE III

Area Percent of Alcohol and Individual Ethylene Oxide Adducts of 1-Dodecanol

| | Example[b] | | | | |
|---|---|---|---|---|---|
| | 17 | 18 | 19 | 20 | 22 |
| Unreacted Alcohol | 1.3 | 1.8 | 1.4 | 2.1 | 1.1 |
| Alcohol[a] | | | | | |
| $E_1$ | 1.1 | 1.3 | 1.8 | 1.5 | .3 |
| $E_2$ | 2.0 | 2.3 | 2.9 | 2.6 | 1.5 |
| $E_3$ | 3.8 | 4.4 | 5.4 | 5.1 | 4.2 |
| $E_4$ | 6.7 | 7.9 | 8.9 | 8.1 | 8.0 |
| $E_5$ | 10.3 | 12.3 | 11.8 | 11.9 | 12.5 |
| $E_6$ | 13.0 | 14.9 | 14.2 | 14.1 | 14.7 |
| $E_7$ | 14.6 | 16.0 | 15.0 | 15.2 | 15.8 |
| $E_8$ | 14.3 | 14.3 | 13.5 | 13.6 | 13.8 |
| $E_9$ | 12.0 | 10.8 | 10.6 | 10.6 | 10.5 |
| $E_{10}$ | 9.2 | 7.1 | 7.0 | 7.3 | 7.0 |
| $E_{11}$ | 6.1 | 4.1 | 4.0 | 4.4 | 4.3 |
| $E_{12}$ | 3.6 | 2.0 | 1.9 | 2.4 | 2.3 |
| $E_{13}$ | 1.7 | 0.8 | 0.7 | 1.0 | .5 |
| $E_{14}$ | 0.4 | | | 0.2 | |
| $E_{15}$ | | | | | |

[a]$E_1$ is the one-mole ethylene oxide adduct, $E_2$ is the two-mole ethylene oxide adduct, etc.
[b]given as an area percent.

EXAMPLE 23

This example shows the use of $H_3PO_4$ as the oxyalkylation promoter and $Ca(OR)_2$ as the oxyalkylation catalyst. To 100 milliliters of absolute ethanol was added 3.5 grams of calcium metal and the mixture was refluxed until all the calcium reacted. LIAL 125 alcohol, (600 grams of a $C_{12}$-$C_{15}$ mixture of primary alcohols, 40% normal, 60% branched, available from Liquichemica Italia), was added to the mixture and the ethanol was removed at 100° and at a pressure of 5 millimeters. Phosphoric acid (4.47 grams) was added to the mixture with stirring. A 589 gram aliquot was reacted with ethylene oxide as in Example 1 with 930 ml of ethylene oxide reacting over a period of 88 minutes to give a nonionic surfactant having a molecular weight of 507 and a cloud point (1 percent aqueous) of less than 25° C.

EXAMPLE 24

This comparative example shows that the use of only sulfuric acid is not effective as an oxyalkylation catalyst. Sulfuric acid (2.45 grams, 0.025 moles) was added with stirring to 1-dodecanol (500 grams). In the autoclave and at the conditions of Example 1 a 496 grams aliquot of this mixture reacted with only 115 milliliters of ethylene oxide over a period of 115 minutes.

EXAMPLE 25

This example shows the use of sulfuric acid as the oxyalkylation promoter, according to this invention, and calcium alkoxide as the oxyalkylation catalyst. To a calcium ethoxide solution prepared by reacting calcium metal (3.48 grams) with 100 milliliters of ethanol after which the mixture was added to 2-ethylhexanol. The ethanol was removed at 65° C. and a pressure of 5 millimeters to give a mixture of calcium alkoxide in 2-ethylhexanol containing 0.152 moles of calcium alkoxide per 1000 grams of the mixture. Sulfuric acid (2.96 grams) was added with stirring. A 594 gram aliquot of the resulting mixture was employed as the oxyalkylation catalyst according to Example 1 and reacted with 1410 milliliters of ethylene oxide over a period of 130 minutes. The oxyalkylation product had a molecular weight of 418 and a cloud point (1 percent aqueous) of 66° C. Gas chromatographic analysis of the trimethylsilyl derivative of the product gave the molecular weight distribution set forth in Table IV.

EXAMPLE 26

This example shows the use of of $H_2SO_4$ as the oxyalkylation promoter and $Ca(OR)_2$ as an oxyalkylation catalyst. Calcium metal (32 grams) was heated under reflux with 1012 milliliters of ethanol until the reaction was complete and then added to 1-dodecanol (800 grams). The ethanol was removed at 100° C. and a pressure of 5 millimeters to give a mixture of calcium alkoxide in 1-dodecanol which contained 1.16 moles of calcium per 1000 grams of the mixture. To 75 grams of the mixture was added 525 grams of 1-dodecanol to give a mixture containing 0.12 moles of calcium per 1000 grams of the mixture. Sulfuric acid (2.45 grams, 0.024 moles), was added to this mixture with stirring. The mixture (589 grams) was employed as in Example 1 with 1045 milliliters of ethylene oxide reacting over a period of 92 minutes to give an ethylene oxide adduct of 1-dodecanol having a molecular weight of 481 and a cloud point (1 percent aqueous) of 54.6° C. Gas chromatographic analysis of the trimethylsilyl derivative gave the molecular distribution set forth in Table V.

EXAMPLE 27

This example shows the use of a higher concentration of $H_2SO_4$ than that employed in Example 26. To a 500 gram mixture of calcium alkoxide in 1-dodecanol (prepared as in Example 26) and containing 0.132 moles of calcium per 1000 grams of the mixture was added, with stirring, 3.24 grams (0.032 mole) of sulfuric acid. The mixture (495 grams) was employed as an oxyalkylation catalyst according to the procedure of Example 1 with 880 milliliters of ethylene oxide reacting over a period of 77 minutes. The product, a poly(ethylene oxide) adduct of 1-dodecanol, had a molecular weight of 488 and a cloud point (1 percent aqueous) of 52.3° C. Gas chromatographic analysis of the trimethylsilyl derivative gave the molecular distribution set forth in Table V.

EXAMPLE 28

This comparative example shows that when p-toluenesulfonic acid is employed as an oxyalkylation catalyst promoter at the same concentration as the sulfuric acid in Example 26 that p-toluenesulfonic acid is not effective as an oxyalkylation promoter catalyst. To a 600 gram mixture of calcium alkoxide in 1-dodecanol (prepared by the procedure of Example 26 and containing 0.12 moles of calcium per 1000 grams) was added 9.32 grams (0.049 mole) of p-toluenesulfonic acid monohydrate. The mixture was employed as an oxyalyation catalyst according to the procedure of Example 1 with 95 milliliters of ethylene oxide reacting over a period of 360 minutes.

EXAMPLE 29

This comparative example shows that when calcium hydroxide is employed as the oxyalkylation catalyst, instead of a calcium alkoxide, that such is not effective as an oxyalkylation catalyst. Calcium hydroxide (5.37 grams, 0.072 mole) was suspended in 1-dodecanol (500 grams). Sulfuric acid (2.42 grams, 0.025 mole) was added to the mixture (with stirring) at 50° C. The mixture was employed as an oxyalkylation catalyst according to the procedure of Example 1 with only 120 milliliters of ethylene oxide reacting over a period of 120 minutes.

EXAMPLE 30

This comparative example shows that when calcium oxide is used as the oxyalkylation catalyst in conjunction with an oxyalkylation promoter according to this invention, instead of a calcium alkoxide, that such is not effective as an oxyalkylation catalyst. Calcium oxide (4.06 grams, 0.072 mole) and sulfuric acid (2.35 grams, 0.024 mole) were added to 1-dodecanol (500 grams) with stirring. The alkylation reaction was carried out as in Example 1 with only 100 milliliters of ethylene oxide reacting with the mixture over a period of 120 minutes.

EXAMPLE 31

This example shows the preparation of an oxyalkylation catalyst according to the invention comprising a calcium alkoxide and sulfuric acid (as the oxyalkylation promoter). Calcium metal (2.9 grams) was added to ethanol (100 milliters) and heated until complete reaction occurred and then added to 500 grams of LIAL-125 alcohol (as in Example 23). The ethanol was removed by heating under vacuum. The final mixture contained 0.145 moles of calcium alkoxide per 1000 grams of the mixture. Sulfuric acid (3.56 grams, 0.036 moles) was then added to the mixture while stirring and 496 grams of the resulting mixture was employed, as in Example 1, with 780 milliliters of ethylene oxide reacting over a period of 96 minutes. The product, a nonionic surfactant, had a molecular weight of 512 and a cloud point (1 percent aqueous) of less than 25° C.

EXAMPLE 32

This example shows the use of a strontium alkoxide and phosphoric acid as the oxyalkylation catalyst. Strontium metal (7.63 grams, 0.087 mole) was reacted with ethanol (100 milliliters) after which the mixture was added to 2-ethylhexanol (600 grams) and the ethanol removed under vacuum. The resulting mixture contained 0.115 moles of strontium alkoxide per 1000 grams of the mixture. Phosphoric acid (2.18 grams, 0.023 moles) was added to the mixture, with stirring, and 591 grams of the resulting mixture was employed as an oxyalkylation catalyst as in Example 1 with 1125 milliters of ethylene oxide reacting over a period of 54 minutes. The product, a poly(ethylene oxide) adduct of 2-ethylhexanol, had a molecular weight of 366 and a cloud point (1 percent aqueous) of 37.8° C. Gas chromatographic analysis of the trimethylsilyl derivative gave the molecular distribution set forth in Table IV.

EXAMPLE 33

This example shows the use of strontium alkoxide and phosphoric acid as the oxyalkylation catalyst. Strontium metal (30.7 grams) was reacted with ethanol (500 grams) after which 1-dodecanol (1900 grams) was added and the ethanol removed under vacuum. The resulting mixture of strontium alkoxide in 1-dodecanol contained 0.133 moles of strontium alkoxide per 1000 grams of the mixture. To a 636 grams aliquot of the mixture was added, phosphoric acid (2.68 grams, 0.027 mole), with stirring. The mixture was then heated to 110° under vacuum. The mixture (630 grams thereof) was then employed as in Example 1 with 1125 milliliters of ethylene oxide reacting over a period of 80 minutes. The product, a poly(ethylene oxide) adduct of 1- dodecanol had a cloud point (1 percent aqueous) of 47.5° C. Gas chromatographic analysis of the trimethylsilyl derivative of the product gave the molecular distribution set forth Table V.

EXAMPLE 34

This example shows the effect of employing a greater concentration of phosphoric acid than that employed in Example 33. To a 600 gram aliquot of the 0.133 mole per 1000 gram mixture of strontium alkoxide in 1-dodecanol of Example 33 was added phosphoric acid (3.83 gram, 0.038 mole), with stirring. After heating the mixture at 110° C. under vacuum a 594 gram aliquot was reacted with ethylene oxide according to the procedure of Example 1 with a period of 54 minutes being required to react 1055 milliters of ethylene oxide. The product had a molecular weight of 507 and a cloud point (1 percent aqueous) of 49.5° C. Gas chromatographic analysis of the trimethylsilyl derivative of the product gave the molecular distribution set forth in Table V.

EXAMPLE 35

This comparative example shows the use of strontium alkoxide as the oxylkylation catalyst without the use of an oxyalkylation promoter. A 618 gram aliquot of the mixture of strontium alkoxide in 1-dodecanol prepared in Example 33 was reacted with ethylene oxide as in Example 33. The rate of reaction was slower than that observed when phosphoric acid was employed according to this invention as an oxyalkylation promoter with a period of 128 minutes being required to react 1100 milliters of ethylene oxide. The product had a molecular weight of 487 and a cloud point (1 percent aqueous) of 48.5° C. Gas chromatographic analysis of the trimethylsilyl derivative of the product gave the molecular distribution set forth in Table V which is a broader molecular distribution that obtained in example 33.

EXAMPLE 36

This comparative example shows that the use of strontium hydroxide and phosphoric acid as the oxyalkylation catalyst is not effective. 1-Dodecanol (600 grams) and strontium hydroxide octahydrate (23.1 grams, 0.087 mole) were heated at 100° C. under a pressure of 5 millimeters of mercury, with stirring. Phosphoric acid (2.76 grams, 0.029 moles) was added and the mixture was again heated to 100° C. under a pressure of 5 millimeters. The mixture was employed according to the procedure of Example 1 with only 65 milliters of ethylene oxide reacting over a period of 360 minutes.

EXAMPLE 37

This comparative example shows that the use of strontium oxide and phosphoric acid is not effective as an oxyalkylation catalyst. 1-Dodecanol (600 grams), strontium oxide (9.02 grams, 0.087 moles) and phosphoric acid (2.76 grams, 0.028 moles) were mixed with the resulting mixture being employed as an oxyalkylation catalyst, as in Example 1, with only 135 milliters of ethylene oxide reacting over a period of 120 minutes.

Example 38

This example shows the production of a commercial-type surfactant by use of the oxyalkylation catalysts of the present invention. To a mixture of strontium alkoxide in 500 grams of LIAL 125 alcohol (prepared by adding strontium ethoxide in ethanol to LIAL 125 alcohol, removing ethanol and obtaining a mixture containing 0.121 moles of strontium alkoxide per 1000 grams) was added phosphoric acid (2.90 grams, 0.0303 moles). A 500 grams aliquot of the resulting mixture was employed according to the procedure of Example 1 with 790 millimeters of ethylene oxide reacting over a period of 33 minutes. The product, a nonionic surfactant, has a molecular weight of 521 and a cloud point (1 percent aqueous) of 46° C.

EXAMPLE 39

This examples shows the use of sulfuric acid and a strontium alkoxide as an oxyalkylation catalyst, according to the present invention. To 2-ethylhexanol (600 grams) was added a mixture of strontium ethoxide in ethanol (prepared by reacting strontium metal (7.6 grams) with ethanol (100 millimeters)). The ethanol was removed under vacuum to give a mixture of strontium alkoxide in 2-ethylhexanol containing 0.186 moles of strontium alkoxide per 1000 grams of the mixture. To this mixture (with stirring) was added sulfuric acid (3.61 grams, 0.037 moles). A 604 gram aliquot of the mixture was reacted with ethylene oxide according to the procedure of Example 1 with a total of 1650 milliters of ethylene oxide reacting over a period of 46 minutes. The product, a poly(ethylene oxide) adduct of 2-ethylhexanol, had a molecular weight of 456 and a cloud point (1 percent aqueous) of 78.2° C. The gas chromatographic analysis of the trimethylsilyl derivative of the product gave the molecular distribution set forth in Table IV.

EXAMPLE 40

This example shows the use of sulfuric acid and strontium alkoxide as the oxyalkylation catalyst, according to the present invention. To a mixture of strontium alkoxide in 1-dodecanol (506 grams containing 0.112 moles of strontium alkoxide per 1000 grams of the mixture and made as in Example 38, with 1-dodecanol, instead of LIAL 125 alcohol) was added, with stirring, sulfuric acid (3.63 grams, 0.037 moles). A 508 gram aliquot was employed as the oxyalkylation catalyst according to the procedure of Example 1 with a period of 78 minutes being required for reaction of 900 millimeters of ethylene oxide. The product, a poly(ethylene oxide) adduct of 1-dodecanol, has a molecular weight of 480 and a cloud point (1 percent aqueous) of 51.5° C. Chromatographic analysis of the trimethylsilyl derivative of the product gave the molecular distribution set forth in Table V.

EXAMPLE 41

This example is a repeat of the oxyalkylation reaction of Example 40. To a 600 gram mixture of strontium alkoxide in 1-dodecanol (containing 0.161 moles of strontium alkoxide per 1000 grams of the mixture and prepared as in Example 40) was added sulfuric acid (4.40 grams, 0.045 moles) with stirring. The mixture was employed as an oxyalkylation catalyst according to the procedure of Example 1 with a 536 gram aliquot of the mixture reacting with 950 milliliters of ethylene oxide over a period of 69 minutes. The resulting product had a molecular weight of 476 and a cloud point (1 percent aqueous) of 49.5° C. Gas chromatographic analysis of the trimethylsilyl derivative of the product is given Table V.

EXAMPLE 42

This comparative example shows that the use of strontium hydroxide and sulfuric acid as the oxyalkylation is not effective as an oxyalkylation catalyst. Strontium hydroxide octahydrate (19.27 grams, 0.072 moles) and sulfuric acid (2.37 grams, 0.024 moles) were added to 500 grams of 1-dodecanol. The resulting mixture was employed according to the procedure of Example 1 with 50 milliliters of ethylene oxide reacting over a period of 125 minutes.

EXAMPLE 43

This comparative example shows that strontium oxide and sulfuric acid are not effective as an oxyalkylation catalyst. Strontium oxide (7.56 grams, 0.073 mole) and sulfuric acid (2.36 grams, 0.024 mole) were added to 500 grams of 1-dodecanol and employed according to the procedure of Example 1. The resulting mixture reacted with 85 milliliters of ethylene oxide over a period of 120 minutes.

EXAMPLE 44

This comparative example shows the use of sulfuric acid with the catalyst disclosed in U.S. Pat. No. 4,223,164 (strontium hydroxide octahydrate). To 1-dodecanol (600 grams) was added (with stirring) 23.1 grams (0.087 mole) of strontium hydroxide octahydrate, 16.4 grams (0.174 moles) of phenol, and then with 2.8 grams (0.29 mole) of sulfuric acid. The mixture was employed according to the procedure of Example 1 with 115 milliliters of ethylene oxide reacting over a period of 120 minutes.

EXAMPLE 45

This example shows the preparation of a nonionic surfactant (using LIAL alcohol) using an oxyalkylation catalyst prepared according to the present invention. A mixture of strontium ethoxide in ethanol (made by reacting 5.7 grams (0.073 mole) of strontium metal with ethanol (100 milliters)) was added to 500 grams of LIAL-125 alcohol (see Example 23), with the ethanol being then removed under vacuum. Sulfuric acid (3.83 grams, 0.039 mole) was added to this mixture and a 500 gram aliquot was employed according to the procedure of Example 1, reacting with 790 milliters of ethylene oxide over a period of 33 minutes. The product, a nonionic surfactant, had a molecular weight of 505.

TABLE IV

Area Percent of Alcohol an Individual Ethylene Oxide Adducts of 2-Ethylhexanol

|  | Example[b] | | | | |
|---|---|---|---|---|---|
|  | 25 | 32 | 39 | 46 | 57 |
| Unreacted Alcohol | 10.9 | 12.9 | 5.3 | 15.7 | 9.0 |
| Alcohol[a] | | | | | |
| $E_1$ | 2.1 | 3.3 | 1.6 | 2.3 | 2.2 |
| $E_2$ | 2.5 | 4.3 | 2.2 | 2.0 | 2.3 |
| $E_3$ | 5.9 | 6.7 | 5.4 | 3.8 | 5.0 |
| $E_4$ | 7.8 | 9.2 | 7.4 | 5.5 | 7.0 |
| $E_5$ | 10.3 | 11.9 | 9.9 | 7.5 | 9.5 |
| $E_6$ | 11.7 | 13.5 | 11.6 | 9.2 | 11.5 |
| $E_7$ | 12.5 | 13.4 | 12.9 | 11.0 | 12.6 |
| $E_8$ | 11.4 | 11.9 | 12.0 | 11.0 | 11.6 |
| $E_9$ | 9.2 | 8.6 | 10.0 | 9.7 | 9.4 |
| $E_{10}$ | 6.6 | 5.4 | 7.7 | 8.0 | 6.9 |
| $E_{11}$ | 4.3 | 3.1 | 5.0 | 6.0 | 4.7 |
| $E_{12}$ | 2.6 | 1.6 | 3.2 | 4.2 | 2.9 |
| $E_{13}$ | 1.4 | 0.7 | 1.7 | 2.5 | 1.4 |
| $E_{14}$ | 0.6 | 0.2 | 0.8 | 1.3 | 0.6 |
| $E_{15}$ | 0.2 |  | 0.2 | 0.4 | 0.1 |
| $E_{16}$ |  |  |  | 0.1 |  |
| $E_{17}$ |  |  |  |  |  |

[a]$E_1$ is the one-mole ethylene oxide adduct, $E_2$ is the two-mole ethylene oxide adduct, etc.
[b]area percent.

TABLE V

Area Percent of Alcohol and Individual Ethylene Oxide Adducts of 1-Dodecanol

|  | Example[b] | | | | | | |
|---|---|---|---|---|---|---|---|
|  | 26 | 27 | 33 | 34 | 35 | 40 | 41 |
| Unreacted Alcohol | 2.3 | 2.8 | 2.2 | 5.2 | 2.6 | 3.7 | 2.9 |
| Alcohol[a] | | | | | | | |
| $E_1$ | 1.2 | 1.5 | 1.6 | 1.8 | 2.1 | 2.0 | 1.9 |
| $E_2$ | 1.8 | 2.2 | 2.8 | 2.3 | 3.8 | 3.0 | 3.2 |
| $E_3$ | 3.6 | 4.1 | 5.7 | 4.1 | 6.6 | 4.8 | 5.7 |
| $E_4$ | 7.6 | 8.4 | 10.0 | 7.6 | 9.4 | 8.1 | 8.8 |
| $E_5$ | 12.4 | 13.4 | 14.7 | 13.3 | 13.2 | 12.1 | 12.4 |
| $E_6$ | 16.7 | 17.2 | 17.2 | 17.5 | 14.7 | 15.6 | 15.3 |
| $E_7$ | 18.3 | 18.1 | 16.2 | 17.6 | 14.4 | 16.2 | 15.6 |
| $E_8$ | 15.4 | 14.4 | 12.7 | 13.6 | 12.2 | 13.5 | 13.3 |
| $E_9$ | 10.6 | 9.4 | 8.5 | 8.5 | 9.2 | 9.6 | 9.6 |
| $E_{10}$ | 6.0 | 5.3 | 4.8 | 4.5 | 6.1 | 6.1 | 6.0 |
| $E_{11}$ | 2.8 | 2.5 | 2.4 | 2.2 | 3.6 | 3.2 | 3.3 |
| $E_{12}$ | 1.0 | 0.8 | 1.0 | 1.1 | 1.8 | 1.5 | 1.6 |
| $E_{13}$ | 0.2 |  | 0.3 | 0.5 | 0.6 | 0.5 | 0.6 |
| $E_{14}$ |  |  |  | 0.2 |  |  |  |

[a]$E_1$ is the one-mole ethylene oxide adduct, $E_2$ is the two-mole ethylene oxide adduct, etc.
[b]area percent.

We claim:

1. The method for the alkoxylation of a reactive hydrogen compound selected from the group consisting of monohydric alcohols having between about 8 and about 25 carbon atoms, both branched and linear, and a difunctional polypropylene oxide polymer having an average molecular weight in the range of 1000 to 5000 comprising contacting said reactive hydrogen compound with an alkylene oxide having between 2 and 4 carbon atoms in the presence of a catalyst selected from the group consisting of calcium alkoxides, strontium alkoxides, calcium phenoxides and strontium phenoxides and an oxyalkylation catalyst promoter selected from the group consisting of superphosphoric acid, phosphoric acid, sulfuric acid, alkali metal and alkaline earth metal dihydrogen phosphates and dihydrogen diphosphates, alkyl, aryl, araalkyl and alkyaryl dihydrogen phosphates, monoalkyl hydrogen sulfates, carbon dioxide, carbonic acid, alkali metal bicarbonates, oxides of phosphorus, sulfur trioxide, sulfur dioxide and sulfurous acid at a temperature between about 50° C. and about 400° C. employing about 2 to about 50 moles of alkylene oxide per mole of reactive hydrogen.

2. The method of claim 1 wherein the oxyalkylation catalyst, promoter is selected from the group consisting of sulfuric acid, sulfurous acid, monoalkyl hydrogen sulfates, sulfur trioxide and sulfur dioxide.

3. The method of claim 1 wherein the catalyst is selected from the group consisting of calcium alkoxide and strontium alkoxide.

4. The method of claim 1 wherein the active hydrogen compound is a product of a hydroformylation/hydrogenation reaction.

5. The method of claim 1 wherein the reaction is carried out at a pressure between about 10 psig and 100 psig.

6. The method of claim 1 wherein the catalyst is present in an amount between about 0.1 and about 1.0 percent by weight based upon the weight of alcohol.

7. The method of claim 1 wherein the reactive hydrogen compound is an alkanol which is a linear alcohol containing between about 8 and about 20 carbon atoms, the alkylene oxide is ethylene oxide, the catalyst is a calcium alkoxide and the oxyalkylation catalyst promoter is phosphoric acid.

8. The method of claim 1 wherein the oxyalkylation catalyst promoter is selected from the group consisting superphosphorus acid, phosphoric acid, oxides of phosphorus, phosphorus acid, alkali metal and alkaline earth metal dihydrogen phosphates and dihydrogen diphosphates.

* * * * *